United States Patent
Kimoto et al.

(10) Patent No.: US 6,714,876 B2
(45) Date of Patent: Mar. 30, 2004

(54) CONTROL SYSTEM

(75) Inventors: Yuji Kimoto, Aichi (JP); Toshiya Matsuoka, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 376 days.

(21) Appl. No.: 09/793,506

(22) Filed: Feb. 27, 2001

(65) Prior Publication Data

US 2001/0032054 A1 Oct. 18, 2001

(30) Foreign Application Priority Data

Feb. 28, 2000 (JP) .................................. 2000-051636

(51) Int. Cl.$^7$ ........................ G06F 19/00; G01N 31/00
(52) U.S. Cl. ............................. 702/24; 702/52; 702/53; 73/861; 73/146; 73/52; 73/47; 204/401; 204/425
(58) Field of Search ............................. 702/24, 52, 53; 73/861, 47, 52, 146, 23.21, 335.05; 701/1; 340/438; 204/401, 425; 280/735

(56) References Cited

U.S. PATENT DOCUMENTS

| | | | |
|---|---|---|---|
| 5,062,065 A | | 10/1991 | Lampe |
| 5,526,280 A | * | 6/1996 | Consadori et al. ............ 702/24 |
| 5,694,118 A | * | 12/1997 | Park et al. .................. 340/632 |
| 5,968,100 A | * | 10/1999 | Kayano et al. ................ 701/1 |
| 5,969,600 A | * | 10/1999 | Tanguay ..................... 340/438 |
| 6,055,848 A | * | 5/2000 | Weigold .................... 73/31.05 |
| 6,059,947 A | * | 5/2000 | Kato et al. .................. 204/425 |
| 6,120,663 A | * | 9/2000 | Kato et al. .................. 204/401 |
| 2002/0121132 A1 | * | 9/2002 | Breed et al. ................. 73/146 |
| 2002/0140214 A1 | * | 10/2002 | Breed et al. ............... 280/735 |

FOREIGN PATENT DOCUMENTS

| | | |
|---|---|---|
| EP | 0 545 647 A1 | 6/1993 |
| JP | 54-118899 | 9/1979 |
| JP | 55-59336 | 5/1980 |
| JP | 2-304342 | 12/1990 |
| JP | 9-304320 | 11/1997 |
| JP | 2001-281185 | 10/2001 |
| JP | 2002-055068 | 2/2002 |

OTHER PUBLICATIONS

European Search Report for EP 01 30 1775 dated Sep. 1, 2003.

* cited by examiner

*Primary Examiner*—John Barlow
*Assistant Examiner*—Aditya S Bhat
(74) *Attorney, Agent, or Firm*—Sughrue Mion, PLLC

(57) ABSTRACT

A control system for a gas sensor element capable of lessening the effect of variations in sensor properties among gas sensor elements as well as the effect of environmental factors, such as temperature and humidity, to thereby accurately detect variation in the concentration of a specific gas. In a control system 10 for a gas sensor element 11 whose sensor resistance Rs varies with the concentration of NOx gas, a pulse signal Sc which alternates between 0 V and +5 V is input to a pulse input terminal 17. When a voltage of 5 V is applied to the pulse input terminal 17, a capacitor 14 is charged via a fixed resistor 15 having a resistance Rc and a diode 16. When a voltage of 0 V is applied, the capacitor 14 discharges via the gas sensor element 11. An output voltage Vout is A/D-converted and processed by means of a microcomputer 20, thereby controlling an electronic control assembly 21. The potential Vout at an operating point Pd varies with the sensor resistance Rs as well as with the duty ratio DT of the pulse signal Sc. Thus, the output voltage Vout can be maintained within a predetermined range by adjusting the duty ratio.

13 Claims, 8 Drawing Sheets

CONTROL SYSTEM

BACKGROUND OF THE INVENTION

1. Field of the Invention

The present invention relates to a control system using a gas sensor element for various control operations, such as controlling the introduction of outside air into the passenger compartment of an automobile by detecting a variation in the concentration of a gas in the environment. More particularly, the invention relates to a control system using a gas sensor element capable of lessening the effect of variations in sensor resistance among gas sensor elements as well as the effect of variation in the sensor resistance of the gas sensor element caused by environmental factors, such as temperature and humidity.

2. Description of the Related Art

Since the sensor resistance of a gas sensor element using a $WO_3$ thin film, lead-phthalocyanine, or $SnO_2$ varies with the concentration of a specific gas, such as NOx, CO, or HC (hydrocarbon) contained in the environment, a conventionally known gas sensor element detects a variation in the concentration of a specific gas as a function of sensor resistance. For example, by using such a gas sensor element, a known control system opens/closes a flap for introducing outside air into the passenger compartment of an automobile according to the condition of contamination of outside air, or controls an air cleaner upon detection of contamination of air within the passenger compartment due to smoking.

In many cases, a control system using such a gas sensor element detects variation in sensor resistance in the form of an electric signal in the following manner. A gas sensor element having a sensor resistance Rs, and a detection resistor having a predetermined detection resistance Rd are connected in series. A predetermined direct-current voltage is applied between opposite ends to thereby divide the voltage by means of the gas sensor element and the detection resistor. On the basis of a divided voltage appearing from a point between the gas sensor element and the detection resistor, various processes are performed.

However, the sensor resistance Rs of a gas sensor element may be greatly influenced by factors, such as temperature and humidity, of the environment in which the gas sensor element is placed, as well as by the concentration of a specific gas, such as NOx, to be detected. Due to environmental factors, such as temperature and humidity, the sensor resistance Rs of the gas sensor element and the detection resistance Rd of a detection resistor may differ greatly in an arrangement where the concentration of a specific gas is determined by detecting a variation in the potential obtained by applying a predetermined voltage to a voltage divider comprising the gas sensor element and the detection resistor as described above. As a result, the potential obtained by the voltage divider may be biased near the predetermined potential or ground potential. Thus, the sensor resistance Rs; i.e., variation in the concentration of a specific gas, cannot be detected accurately.

Also, since sensor properties are not completely uniform among gas sensor elements, even when similar gas sensor elements are used, the sensor resistance Rs; i.e., an output, may vary among the gas sensor elements.

SUMMARY OF THE INVENTION

An object of the invention is to provide a control system using a gas sensor element capable of lessening the effect of variations in sensor properties among gas sensor elements as well as the effect of environmental factors, such as temperature and humidity, to thereby accurately detect variation in the concentration of a specific gas.

To achieve the above object, the present invention provides a control system for a gas sensor element whose sensor resistance varies with the concentration of a specific gas, comprising: a pulse input point into which a pulse signal is input in a repetitive waveform having a first potential state and a second potential state; a capacitor; a charging circuit for charging the capacitor via a charge resistor during a period when the pulse signal in the first potential state is input to the pulse input point; and a discharging circuit for discharging the capacitor via a discharge resistor during a period when the pulse signal in the second potential state is input to the pulse input point. The gas sensor element having a sensor resistance comprises at least either the charge resistor of the charging circuit or the discharge resistor of the discharging circuit. Furthermore, at least either the charging current of the charging circuit or discharging current of the discharging circuit varies with the sensor resistance of the gas sensor element. The control system further comprises a control circuit, which in turn comprises a microcomputer; and an A/D converter circuit for converting a potential at an operating point located at one end of the capacitor to a digital valve, which potential varies with the sensor resistance of the gas sensor element. The control circuit is connected to the pulse input point and outputs the pulse signal.

In the control system using a gas sensor element of the above embodiment, the capacitor is charged and discharged by means of the pulse signal. Also, at least either the charging current during charging or discharging current during discharge varies with the sensor resistance of the gas sensor element. The voltage across the capacitor becomes steady by repeated charging and discharging according to the pulse signal, and the charging voltage of the capacitor (a voltage as measured across the capacitor) varies with the sensor resistance. Thus, when the sensor resistance of the gas sensor element varies as a result of the gas sensor element detecting the specific gas, the charging voltage of the capacitor varies accordingly. As a result, the potential of the operating point located at one end of the capacitor varies accordingly. Thus, an A/D-converted value of the potential varies according to the concentration of the specific gas. Therefore, variation in the concentration of the specific gas can be known from the A/D-converted value.

In the control system, the charging voltage of the capacitor can be varied by varying the duty ratio or the amplitude (the difference between the first potential and the second potential) of the pulse signal, which is output from the control circuit and is input to the pulse input point. Accordingly, when the sensor resistance of the gas sensor element varies due to variation in environmental factors, such as temperature or humidity, the duty ratio, for example, of the pulse signal is varied appropriately to prevent large biasing of the potential at the operating point or an A/D-converted value of the potential, thereby maintaining the value within an appropriate range. Thus, even in this case, variation in the potential at the operating point associated with variation in the concentration of the specific gas can be reliably determined. Similarly, even when sensor properties, such as sensor resistance (for example, a sensor resistance as obtained in an environment of a standard gas concentration at predetermined temperature and humidity), vary among gas sensor elements, the duty ratio, for example, of the pulse signal is varied appropriately in order to prevent large biasing of the potential at the operating point (an A/D-converted value of the potential), thereby maintaining the value within an appropriate range. Thus, variation in the potential at the operating point associated with variation in the concentration of the specific gas can be determined.

The pulse signal is not particularly limited, so long as the pulse signal has a waveform which alternates between a first potential state and a second potential state. The first potential and the second potential may be set for use with a single-polarity power source; for example, either the first potential or the second potential assumes +5V, whereas the other assumes 0 V (ground). Alternatively, the first potential and the second potential may be set for use with a dual-polarity power source; for example, either the first potential or the second potential assumes +5V, whereas the other assumes −5 V. In order to vary the potential at the operating point, PMW (pulse width modulation) or amplitude modulation for varying the duty ratio of the pulse signal is employed.

The charging circuit is not particularly limited, so long as the charging circuit can charge the capacitor according to the pulse signal in the first potential state which is input to the pulse input point. The discharging circuit is not particularly limited, so long as the discharging circuit can discharge the capacitor according to the pulse signal in the second potential state which is input to the pulse input point.

However, the charging circuit and the discharging circuit must be configured such that at least either the charging current of the charging circuit or the discharging current of the discharging circuit varies with the sensor resistance of the gas sensor element. For example, the charging circuit may assume the form of a CR series circuit composed of a charge resistor having a resistance Rc and a capacitor having a capacitance C, which are connected in series, and having a first time constant τ1 of CRc. The discharging circuit may assume the form of a CR series circuit composed of a discharge resistor having a resistance Rd and a capacitor having a capacitance C, which are connected in series, and having a second time constant τ2 of CRd. Alternatively, an active element, such as a transistor, an FET, or an operational amplifier, may be used to cause current to flow into or out of the capacitor according to the sensor resistance of the gas sensor element or the resistance of a resistor, to thereby charge or discharge the capacitor.

The charging circuit may be configured such that charging current flows into the capacitor through the pulse input point or such that charging current flows into the capacitor from a separate power source via a switching element, which is driven by an input pulse signal.

The discharging circuit may be configured such that discharging current flows from the capacitor toward the pulse input point or such that the capacitor discharges via a switching element, which is driven by an input pulse signal.

The A/D converter circuit may be configured so as to directly A/D convert the potential at one end of the capacitor or such that a buffer circuit is disposed at a stage preceding A/D conversion. Alternatively, a low-pass filter (LPF) having a cut-off frequency lower than a frequency fp of the pulse signal to be input, or a band elimination filter (BEF) for cutting off signals having frequencies in the vicinity of the frequency of the pulse signal may be disposed at a stage preceding A/D conversion.

In particular, by sufficiently shortening the repetition period Tp of the pulse signal; i.e., by increasing the frequency fp, rippling decreases, whereby the potential at one end of the capacitor (at the operating point) becomes substantially constant. Thus, even when the potential at the operating point is directly A/D-converted, the A/D-converted value is not susceptible to fluctuations associated with charging and discharging. Therefore, an LPF or a like component becomes unnecessary.

That is, preferably, the control system is configured in the following manner. The frequency of the pulse signal is determined such that, within the range of variations in the sensor resistance of the gas sensor element, the maximum ripple value arising in the potential at the operating point becomes smaller than the resolution of the A/D converter circuit. The A/D converter circuit directly converts the potential at the operating point to a digital signal.

A resistor other than the gas sensor element which can be used as the charge resistor or the discharge resistor is a fixed resistor, which has a constant resistance. Alternatively, a variable resistor can be used. The variable resistor can accommodate a sensor resistance Rs which varies over a range of several orders of magnitude, by appropriately modifying its resistance. Variations in properties among gas sensor elements can be compensated by adjusting the resistance of the variable resistor. Further alternatively, another gas sensor element having different properties; for example, a gas sensor element whose resistance varies in response to a gas different from the above-mentioned specific gas, can be used as the charge resistor or the discharge resistor.

Preferably, a control system using a gas sensor element whose sensor resistance varies with the concentration of a specific gas comprises a pulse input point into which a pulse signal is input in a repetitive waveform having a first potential state and a second potential state; a capacitor; a charging circuit for charging the capacitor at a first time constant via a charge resistor during a period when the pulse signal in the first potential state is input to the pulse input point; and a discharging circuit for discharging the capacitor at a second time constant via a discharge resistor during a period when the pulse signal in the second potential state is input to the pulse input point. The gas sensor element having the sensor resistance comprises at least either the charge resistor of the charging circuit or the discharge resistor of the discharging circuit, and at least either the first time constant or the second time constant varies with the sensor resistance of the gas sensor element. The control system further comprises a control circuit, which in turn comprises a microcomputer; and an A/D converter circuit for converting a potential at an operating point located at one end of the capacitor to a digital signal, which potential varies with the sensor resistance of the gas sensor element. The control circuit is connected to the pulse input point and outputs the pulse signal.

The control system for a gas sensor element of the above embodiment is similar to that described previously, but is characterized in that the capacitor is charged or discharged by means of the pulse signal and that at least either the first time constant, which is a time constant for charging, or the second time constant, which is a time constant for discharging, varies with the sensor resistance of the gas sensor element. Accordingly, by repeatedly charging and discharging according to the pulse signal, the voltage across the capacitor becomes steady, and the charging voltage of the capacitor varies with the sensor resistance. Thus, when the gas sensor element detects the specific gas with a resultant variation in the sensor resistance thereof, the charging voltage of the capacitor varies accordingly; as a result, the potential at the operating point varies accordingly. Therefore, an A/D-converted value of the potential varies according to the concentration of the specific gas. Hence, variation in the concentration of the specific gas can be known from the A/D-converted value.

The charging circuit is not particularly limited, so long as the charging circuit can charge the capacitor according to the pulse signal in the first potential state which is input to the pulse input point. The discharging circuit is not particularly limited, so long as the discharging circuit can discharge the capacitor according to the pulse signal in the second potential state which is input to the pulse input point. However, the charging circuit and the discharging circuit must be configured such that at least either the first time constant of the charging circuit or the second time constant of the discharging circuit varies with the sensor resistance of the gas sensor element.

Although the A/D converter circuit may be configured so as to directly convert the potential at the operating point to a digital value, a buffer circuit may be disposed at a stage preceding to A/D conversion, and an LPF having a cut-off frequency lower than a frequency fp of the pulse signal or a BEF for cutting off frequencies in the vicinity of the frequency of the pulse signal may be interposed.

In particular, by sufficiently shortening the repetition period Tp of the pulse signal as compared with the first time constant $\tau 1$ and the second time constant $\tau 2$ (Tp<<$\tau 1$; Tp<<$\tau 2$), a potential at one end of the capacitor (at the operating point) becomes substantially constant. Thus, even when the potential at one end of the capacitor is directly A/D-converted, the A/D-converted value becomes unsusceptible to fluctuations associated with charging and discharging. Therefore, an LPF or a like component, becomes unnecessary. That is, preferably, the control system is configured in the following manner. The repetition period Tp of the pulse signal assumes a value sufficiently smaller than the first time constant $\tau 1$ and the second time constant $\tau 2$. The A/D converter circuit directly converts the potential at the operating point to a digital value.

The present invention further provides a control system for a gas sensor element whose sensor resistance varies with the concentration of a specific gas, comprising: a pulse input point into which a pulse signal is input in a repetitive waveform having a first potential state and a second potential state; a capacitor; a charging circuit for charging the capacitor at a first time constant via a charge resistor during a period when the pulse signal in the first potential state is input to the pulse input point; a discharging circuit for discharging the capacitor at a second time constant via a discharge resistor during a period when the pulse signal in the second potential state is input to the pulse input point, the gas sensor element having the sensor resistance comprises the discharge resistor, and the second time constant varying with the sensor resistance; and a control circuit. The control circuit comprises a microcomputer; and an A/D converter circuit into which is input a potential at an operating point located at one end of the capacitor, which potential varies with the sensor resistance of the gas sensor element. The control circuit is connected to the pulse input point and outputs the pulse signal.

In the control system for a gas sensor element of the above embodiment, the capacitor is charged or discharged by means of the pulse signal, and the second time constant, which is a time constant for discharging, varies with the sensor resistance of the gas sensor element. Accordingly, by repeatedly charging and discharging according to the pulse signal, the voltage across the capacitor becomes steady. Furthermore, the charging voltage of the capacitor varies with the sensor resistance. Thus, when the gas sensor element detects the specific gas with a resultant variation in the sensor resistance thereof, the charging voltage of the capacitor varies accordingly; as a result, the potential at the operating point located at one end of the capacitor varies accordingly. Therefore, an A/D-converted value of the potential varies according to the concentration of the specific gas. Hence, variation in the concentration of the specific gas can be known from the A/D-converted value.

Furthermore, in the control system, the charging voltage of the capacitor can be varied by varying the duty ratio or the amplitude of the pulse signal, which is input to the pulse input point from the control circuit. Accordingly, when the sensor resistance of the gas sensor element varies due to environmental factors, the duty ratio, for example, of the pulse signal is varied appropriately in order to prevent large biasing of the potential at the operating point, thereby maintaining the potential within an appropriate range. Thus, variation in the potential at the operating point associated with variation in the concentration of the specific gas can be reliably determined. Similarly, even when sensor properties vary among gas sensor elements, the duty ratio, for example, of the pulse signal is varied appropriately in order to prevent large biasing of the potential at the operating point, thereby maintaining the potential within an appropriate range. Thus, variation in the potential at the operating point associated with variation in the concentration of the specific gas can be reliably determined.

The present invention still further provides a control system for a gas sensor element whose sensor resistance varies with the concentration of a specific gas, comprising: a pulse input point into which a pulse signal is input in a repetitive waveform having a first potential state and a second potential state; a capacitor; a charging circuit for charging the capacitor at a first time constant via a charge resistor during a period when the pulse signal in the first potential state is input to the pulse input point, the gas sensor element having the sensor resistance comprising the charge resistor, and the first time constant varying with the sensor resistance; a discharging circuit for discharging the capacitor at a second time constant via a discharge resistor during a period when the pulse signal in the second potential state is input to the pulse input point; and a control circuit. The control circuit comprises a microcomputer; and an A/D converter circuit into which is input a potential at an operating point located at one end of the capacitor, which potential varies with the sensor resistance of the gas sensor element. The control circuit is connected to the pulse input point and outputs the pulse signal.

In the control system using a gas sensor element of the above embodiment, the capacitor is charged or discharged by means of the pulse signal, and the first time constant, which is a time constant of charging, varies with the sensor resistance of the gas sensor element. Accordingly, by repeatedly charging and discharging according to the pulse signal, the voltage across of the capacitor becomes steady. Furthermore, the charging voltage of the capacitor varies with the sensor resistance. Thus, when the gas sensor element detects the specific gas with a resultant variation in the sensor resistance thereof, the charging voltage of the capacitor varies accordingly; as a result, the potential at the operating point located at one end of the capacitor varies accordingly. Therefore, an A/D-converted value of the potential varies according to the concentration of the specific gas. Hence, variation in the concentration of the specific gas can be known from the A/D-converted value.

Furthermore, in the control system, the charging voltage of the capacitor can be varied by varying the duty ratio or the amplitude of the pulse signal, which is input to the pulse input point from the control circuit. Accordingly, when the sensor resistance of the gas sensor element varies due to environmental factors, the duty ratio, for example, of the pulse signal is varied appropriately in order to prevent large biasing of the potential at the operating point (an A/D-converted value of the potential), thereby maintaining the potential within an appropriate range. Thus, variation in the potential at the operating point associated with variation in the concentration of the specific gas can be reliably determined. Similarly, even when sensor properties vary among gas sensor elements, the duty ratio, for example, of the pulse signal is varied appropriately in order to prevent large biasing of the potential at the operating point, thereby maintaining the potential within an appropriate range. Thus, variation in the potential at the operating point associated with variation in the concentration of the specific gas can be reliably determined.

The present invention still further provides a control system for a gas sensor element whose sensor resistance varies with the concentration of a specific gas, comprising: a pulse input point into which a pulse signal is input in a repetitive waveform having a first potential state and a second potential state; a capacitor; a charging circuit for charging the capacitor at a first time constant via a resistor and a diode during a period when the pulse signal in the first potential state is input to the pulse input point; a discharging circuit for discharging the capacitor at a second time constant via the gas sensor element during a period when the pulse signal in the second potential state is input to the pulse input point; and a control circuit. The control circuit comprises a microcomputer; and an A/D converter circuit into which is input a potential at an operating point located at one end of the capacitor, which potential varies with the sensor resistance of the gas sensor element. The control circuit is connected to the pulse input point of the charging circuit and outputs the pulse signal.

In the control system using a gas sensor element of the above embodiment, the capacitor is charged via the resistor and the diode during a period when the pulse signal in the first potential state is input; and the capacitor is discharged via the gas sensor element; i.e., via the sensor resistance which varies with the concentration of a gas, during a period when the pulse signal in the second potential state is input. Accordingly, the first time constant for charging is determined by the resistance of the resistor, whereas the second time constant for discharging varies with the sensor resistance. By repeatedly charging and discharging according to the pulse signal, the voltage across of the capacitor becomes steady. Furthermore, the charging voltage of the capacitor varies with the sensor resistance. Thus, when the gas sensor element detects the specific gas with a resultant variation in the sensor resistance thereof, the charging voltage of the capacitor varies accordingly; as a result, the potential at the operating point located at one end of the capacitor varies accordingly. Therefore, an A/D-converted value of the potential varies according to the concentration of the specific gas. Hence, variation in the concentration of the specific gas can be known from the A/D-converted value.

Furthermore, in the control system, the charging voltage of the capacitor can be varied by varying the duty ratio or the amplitude of the pulse signal. Accordingly, when the sensor resistance of the gas sensor element varies due to environmental factors, the duty ratio, for example, of the pulse signal is varied appropriately in order to prevent large biasing of the potential at the operating point, thereby maintaining the potential within an appropriate range. Thus, variation in the potential at the operating point associated with variation in the concentration of the specific gas can be reliably determined. Similarly, even when sensor properties vary among gas sensor elements, the duty ratio, for example, of the pulse signal is varied appropriately in order to prevent biasing of the potential at the operating point, thereby maintaining the potential within an appropriate range. Thus, variation in the potential at the operating point associated with variation in the concentration of the specific gas can be determined.

The present invention still further provides a control system for a gas sensor element whose sensor resistance varies with the concentration of a specific gas, comprising: a pulse input point into which a pulse signal is input in a repetitive waveform having a first potential state and a second potential state; a capacitor; a charging circuit for charging the capacitor at a first time constant via the gas sensor element and a diode during a period when the pulse signal in the first potential state is input to the pulse input point; a discharging circuit for discharging the capacitor at a second time constant via a resistor during a period when the pulse signal in the second potential state is input to the pulse input point; and a control circuit. The control circuit comprises a microcomputer; and an A/D converter circuit into which is input a potential at an operating point located at one end of the capacitor, which potential varies with the sensor resistance of the gas sensor element. The control circuit is connected to the pulse input point of the charging circuit and outputs the pulse signal.

In the control system using a gas sensor element of the above embodiment, the capacitor is charged via the gas sensor element and the diode; i.e., via the sensor resistance which varies with the concentration of a gas, during a period when the pulse signal in the first potential state is input; and the capacitor is discharged via the resistor during a period when the pulse signal in the second potential state is input. Accordingly, the second time constant for discharging is determined by the resistance of the resistor, whereas the first time constant for charging varies with the sensor resistance. Thus, by repeatedly charging and discharging according to the pulse signal, the voltage across the capacitor becomes steady. Furthermore, the charging voltage of the capacitor varies with the sensor resistance. When the gas sensor element detects the specific gas with a resultant variation in the sensor resistance thereof, the charging voltage of the capacitor varies accordingly; as a result, the potential at the operating point located at one end of the capacitor varies accordingly. Therefore, an A/D-converted value of the potential varies according to the concentration of the specific gas. Hence, variation in the concentration of the specific gas can be known from the A/D-converted value.

Furthermore, in the control system, the charging voltage of the capacitor can be varied by varying the duty ratio or the amplitude of the pulse signal. Accordingly, when the sensor resistance of the gas sensor element varies due to environmental factors, the duty ratio, for example, of the pulse signal is varied appropriately in order to prevent large biasing of the potential at the operating point, thereby maintaining the potential within an appropriate range. Thus, variation in the potential at the operating point associated with variation in the concentration of the specific gas can be reliably determined. Similarly, even when sensor properties vary among gas sensor elements, the duty ratio, for example, of the pulse signal is varied appropriately in order to prevent biasing of the potential at the operating point, thereby maintaining the potential within an appropriate range. Thus, variation in the potential at the operating point associated with variation in the concentration of the specific gas can be determined.

The present invention still further provides a control system for a gas sensor element whose sensor resistance varies with the concentration of a specific gas, comprising: a pulse input point into which a pulse signal is input in a repetitive waveform having a first potential state and a second potential state; a capacitor; a charging circuit for charging the capacitor at a first time constant via a RD series circuit comprising a resistor and a first diode, which is connected to the resistor in series, during a period when the pulse signal in the first potential state is input to the pulse input point; a discharging circuit for discharging the capacitor at a second time constant via a SD series circuit comprising the gas sensor element and a second diode, which is connected to the gas sensor element in series, and connected to the RD series circuit in parallel, during a period when the pulse signal in the second potential state is input to the pulse input point; and a control circuit. The control circuit comprises a microcomputer; and an A/D converter circuit into which is input a potential at an operating point located at one end of the capacitor, which potential varies with the sensor resistance of the gas sensor element. The control circuit is connected to the pulse input point of the charging circuit and outputs the pulse signal.

In the control system using a gas sensor element of the above embodiment, the capacitor is charged via the RD series circuit comprising the resistor and the first diode during a period when the pulse signal in the first potential state is input. The capacitor is discharged via the SD series circuit comprising the gas sensor element and the second diode; i.e., via the sensor resistance which varies with the concentration of a gas, during a period when the pulse signal in the second potential state is input. Accordingly, the first time constant for charging is determined by the resistance of the resistor, whereas the second time constant for discharging varies with the sensor resistance. Thus, by repeatedly charging and discharging according to the pulse signal, the voltage across the capacitor becomes steady. Furthermore, the charging voltage of the capacitor varies with the sensor resistance. When the gas sensor element detects the specific gas with a resultant variation in the sensor resistance thereof, the charging voltage of the capacitor varies accordingly; as a result, the potential at the operating point located at one end of the capacitor varies accordingly. Therefore, an A/D-converted value of the potential varies according to the concentration of the specific gas. Hence, variation in the concentration of the specific gas can be known from the A/D-converted value.

Furthermore, in the control system, the charging voltage of the capacitor can be varied by varying the duty ratio or the amplitude of the pulse signal. Accordingly, when the sensor resistance of the gas sensor element varies due to environmental factors, the duty ratio, for example, of the pulse signal is varied appropriately in order to prevent large biasing of the potential at the operating point, thereby maintaining the potential within an appropriate range. Thus, variation in the potential at the operating point associated with variation in the concentration of the specific gas can be reliably determined. Similarly, even when sensor properties vary among gas sensor elements, the duty ratio, for example, of the pulse signal is varied appropriately in order to prevent biasing of the potential at the operating point, thereby maintaining the potential within an appropriate range. Thus, variation in the potential at the operating point associated with variation in the concentration of the specific gas can be determined.

The present invention still further provides a control system for a gas sensor element whose sensor resistance varies with the concentration of a specific gas, comprising: a pulse input point into which a pulse signal is input in a repetitive waveform having a first potential state and a second potential state; a capacitor; a charging circuit for charging the capacitor at a first time constant via a SD series circuit comprising the gas sensor element and a first diode, which is connected to the gas sensor element in series, during a period when the pulse signal in the first potential state is input to the pulse input point; a discharging circuit for causing the capacitor at a second time constant via a RD series circuit comprising a resistor and a second diode, which is connected to the resistor in series, and connected to the SD series circuit in parallel, during a period when the pulse signal in the second potential state is input to the pulse input point; and a control circuit. The control circuit comprises a microcomputer; and an A/D converter circuit into which is input a potential at an operating point located at one end of the capacitor, which potential varies with the sensor resistance of the gas sensor element. The control circuit is connected to the pulse input point of the charging circuit and outputs the pulse signal.

In the control system using a gas sensor element of the present invention, the capacitor is charged via the SD series circuit comprising the gas sensor element and the first diode; i.e., via the sensor resistance which varies with the concentration of a gas, during a period when the pulse signal in the first potential state is input. The capacitor is discharged via the RD series circuit comprising the resistor and the second diode during a period when the pulse signal in the second potential state is input. Accordingly, the second time constant for discharging is determined by the resistance of the resistor, whereas the first time constant for charging varies with the sensor resistance. Thus, by repeatedly charging and discharging according to the pulse signal, the voltage across the capacitor becomes steady. Furthermore, the charging voltage of the capacitor varies with the sensor resistance. When the gas sensor element detects the specific gas with a resultant variation in the sensor resistance thereof, the charging voltage of the capacitor varies accordingly; as a result, the potential at the operating point located at one end of the capacitor varies accordingly. Therefore, an A/D-converted value of the potential varies according to the concentration of the specific gas. Hence, variation in the concentration of the specific gas can be known from the A/D-converted value.

Furthermore, in the control system, the charging voltage of the capacitor can be varied by varying the duty ratio or the amplitude of the pulse signal. Accordingly, when the sensor resistance of the gas sensor element varies due to environmental factors, the duty ratio, for example, of the pulse signal is varied appropriately in order to prevent large biasing of the potential at the operating point, thereby maintaining the potential within an appropriate range. Thus, variation in the potential at the operating point associated with variation in the concentration of the specific gas can be reliably determined. Similarly, even when sensor properties vary among gas sensor elements, the duty ratio, for example, of the pulse signal is varied appropriately in order to prevent biasing of the potential at the operating point, thereby maintaining the potential within an appropriate range. Thus, variation in the potential at the operating point associated with variation in the concentration of the specific gas can be determined.

Preferably, in either of the above-mentioned two control systems, the second potential state is lower in potential than the first potential state, and the pulse input point is connected directly to the RD series circuit and the SD series circuit.

As a result, system configuration becomes simple, to thereby provide an inexpensive control system.

Preferably, in any one of the above-mentioned control systems, either the first potential state or the second potential state is a ground potential state, and the other state is a positive potential state, which is higher in potential than the ground potential.

One potential state of the pulse signal, which is output from the control circuit and input to the pulse input point, assumes the ground potential, and the other potential state assumes a potential higher than the ground potential. Thus, the control system can be powered by a single-polarity power source, thereby simplifying a power circuit for the system.

Preferably, in any one of the above-mentioned control systems, the control circuit further comprises: output range judgement means for judging whether or not an A/D-converted value produced in the A/D converter circuit falls outside a predetermined range; and duty ratio modification means for modifying the duty ratio of the pulse signal such that the A/D-converted value falls within the predetermined range (namely, when the A/D-converted value falls outside the predetermined range).

When the sensor resistance of a gas sensor element varies greatly due to variation in environmental factors, such as temperature or humidity, the A/D-converted value produced in the A/D converter circuit varies greatly. In this state, variation in the sensor resistance derived from variation in the concentration of the specific gas cannot be reliably detected.

By contrast, in the control system of the present invention, when the A/D-converted value falls outside a predetermined range, the duty ratio of the pulse signal is modified such that the A/D-converted value falls within the predetermined range. Accordingly, even when an environmental factor, such as temperature or humidity, varies, the A/D-converted value is maintained within the predetermined range without biasing. Thus, variation in the sensor resistance derived from variation in the concentration of the specific gas can be reliably detected.

Figure 1:
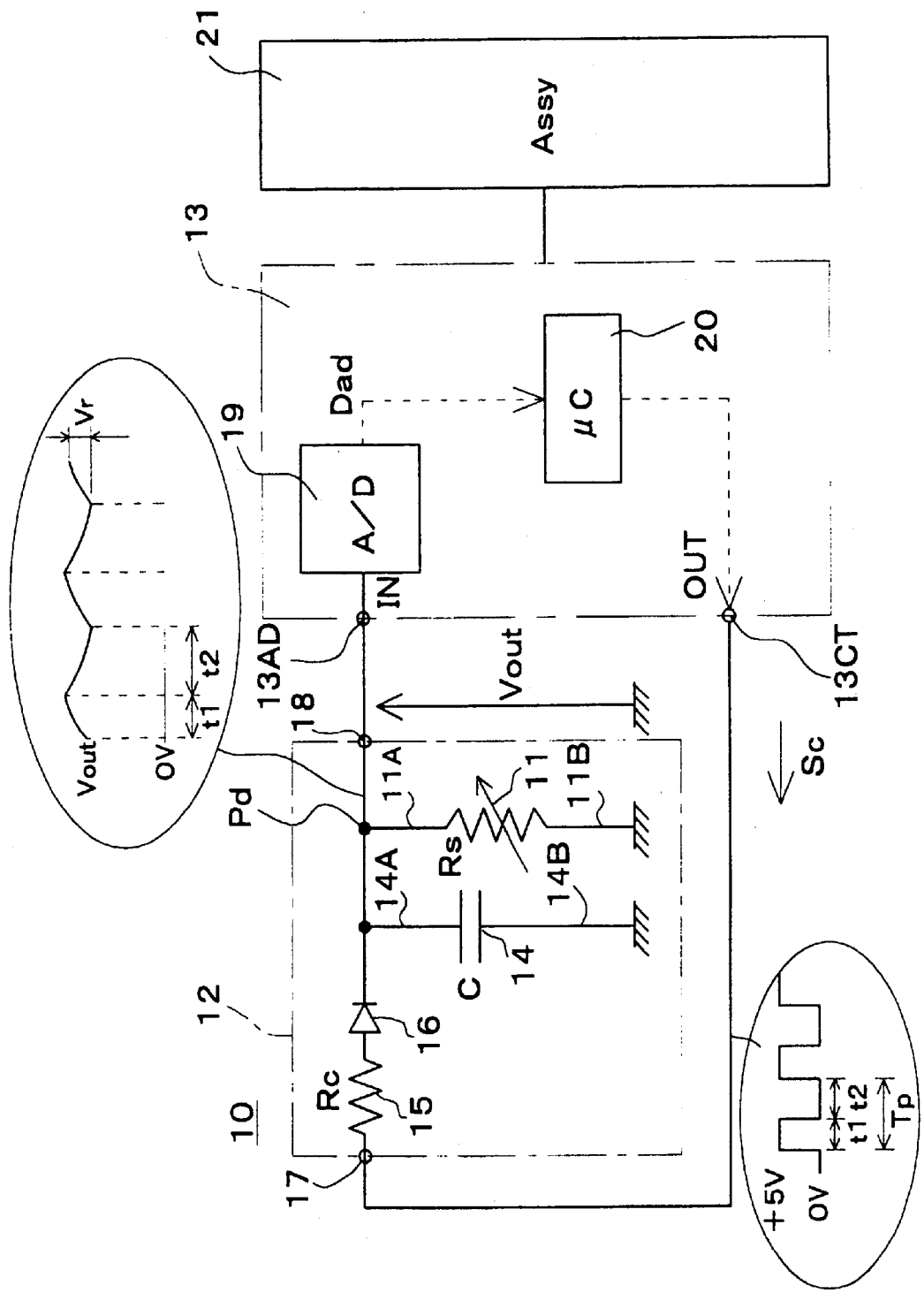
FIG. 1 is a circuit diagram and block diagram showing the configuration of a control system using a gas sensor drive circuit and a gas sensor element according to a first embodiment of the present invention.

Reference numerals are used to identify items shown in the drawings as follows:
10, 50, 60, 70: control systems
11, 51, 61, 71: gas sensor elements
12, 52, 62, 72: gas sensor element drive circuits
13: control circuit
14, 64: capacitors
15, 55, 66, 76: fixed resistors
16: diode
67: first diode
65: second diode
17, 88: pulse input terminals (pulse input points)
19: A/D converter circuit
20: microcomputer
21: electronic control assembly

DESCRIPTION OF THE PREFERRED EMBODIMENTS

The invention will now be described with reference to the drawings. However, the present invention should not be construed as being limited thereto.

A first embodiment of the present invention will next be described with reference to FIGS. 1 to 4. The circuit diagram and a block diagram of FIG. 1 show a control system 10 according to the first embodiment. The control system 10 includes a gas sensor element drive circuit 12 and a control circuit 13. The gas sensor element drive circuit 12 includes a gas sensor element 11 which is formed of an oxide semiconductor and whose sensor resistance Rs varies with the concentration of a specific gas; specifically, the sensor resistance Rs increases with the concentration of an oxidizing gas, such as NOx. The gas sensor element 11 used in the present embodiment is such that the sensor resistance Rs usually varies over a range of 50 k$\Omega$ to 5 M$\Omega$ upon variation in the concentration of the specific gas or environmental factors, such as temperature or humidity.

The gas sensor element drive circuit 12 drives the gas sensor element 11 to thereby obtain a voltage (an output voltage Vout) at an operating point, which will be described later, associated with variation in the sensor resistance Rs of the gas sensor element 11. The gas sensor element drive circuit 12 includes a pulse input terminal (a pulse input point) 17, to which a pulse signal Sc, which will be described later, is input, and an output terminal 18. A fixed resistor 15 having a resistance Rc (7.5 k$\Omega$ in the present embodiment) and a diode 16 are connected in series to the pulse input terminal 17. One end 14B of a capacitor 14 having a capacitance C (3.3 $\mu$F in the present embodiment) is grounded, whereas the other end 14A of the capacitor 14 is connected to the pulse input terminal 17 via the series circuit. The gas sensor element 11 is disposed in parallel with the capacitor 14. One end 11B of the gas sensor element 11 is grounded, whereas the other end 11A of the gas sensor element 11 is connected to the other end 14A of the capacitor 14. The connection point serves as an operating point Pd, whose potential varies with the sensor resistance Rs. The potential at the operating point Pd is fed to the output terminal 18. The diode 16 is oriented such that the cathode thereof is located on the capacitor 14 side.

The control circuit 13 internally includes an A/D converter circuit 19 and a microcomputer 20. The microcomputer 20 includes a microprocessor having a known configuration and adapted to perform arithmetic operations, a RAM for temporarily storing programs and data, and a ROM for retaining programs and data, and may, in some cases, include the A/D converter circuit 19. The output voltage Vout, which is output from the gas sensor element drive circuit 12, is input to an A/D conversion input terminal 13AD and is converted in the A/D converter circuit 19 at predetermined intervals (every 0.4 sec in the present embodiment), to a digital A/D-converted value Dad. The microprocessor 20 processes the A/D-converted value Dad to thereby detect variation in the concentration of NOx gas from the sensor resistance Rs of the gas sensor element 11 and variation in the sensor resistance Rs. The A/D converter circuit converts a potential of 0 V to 5 V into an 8-bit digital value and has a resolution of about 20 mV ($\cong 5$ V/$2^8$=19.5 mV).

As illustrated schematically, an electronic control assembly 21 is connected to the control circuit 13. The control circuit 13 controls the electronic control assembly 21 according to variation in the concentration of the specific gas determined by the above calculation. Examples of the electronic control assembly 21 include a flap control assembly for closing/opening a flap for introduction of outside air into the passenger compartment of an automobile and an air cleaner control assembly for turning on/off an air cleaner for cleaning the air within the passenger compartment of an automobile. For example, the flap control assembly controls motor operation in response to an instruction from the control circuit 13 so as to close an outside-air intake path by means of a flap or to open the outside-air intake path.

Furthermore, the control circuit 13 outputs a pulse signal Sc from a control output terminal 13CT thereof according to, for example, the A/D-converted value Dad. The pulse signal Sc drives the gas sensor element drive circuit 12. As shown in a circle located at a lower position of FIG. 1, the pulse signal Sc alternates a potential of 0 V (ground potential) and a potential of +5 V and has a repetition frequency fp (fp=2 kHz in the present embodiment). The +5 V potential (first potential) continues for a time t1, whereas the 0 V potential (second potential) continues for a time t2. Accordingly, the duty ratio DT (%) of the pulse signal Sc is expressed as DT=100 t1/(t1+t2). The sum of t1 and t2 is a repetition period Tp (=t1+t2). In the present embodiment, an open drain terminal of the microcomputer 20 serves as the control output terminal 13CT. The control system 10 is driven by means of a +5 V single-polarity power source.

When the first potential (high level), or +5 V, of the pulse signal Sc is applied to the input terminal 17, the diode 16 goes ON to thereby charge the capacitor 14 via the fixed resistor 15 and the diode 16. That is, the fixed resistor 15 and the diode 16 constitute a charging circuit for charging the capacitor 14 when the pulse input terminal 17 is in the first potential state. Accordingly, during the period t1, the voltage across the capacitor 14 (charging voltage) rises. A charging time constant (first time constant) τ1 is expressed as τ1=C·Rc·Rs/(Rc+Rs).

When the second potential (low level), or 0 V, of the pulse signal Sc is applied to the input terminal 17, the diode 16 goes OFF to thereby cause the capacitor 14 to discharge the accumulated charge via the gas sensor element 11. That is, the gas sensor element 11 connected in parallel with the capacitor 14 constitutes a discharge circuit for discharging the capacitor 14 when the pulse input terminal 17 is in the second potential state. Accordingly, during the period t2, the voltage across the capacitor 14 (charging voltage) decreases. A discharging time constant (second time constant) τ2 is expressed as τ2=CRs.

Since the gas sensor element drive circuit 12 operates as described above, by repeated input of the pulse signal Sc, a steady state arises; i.e., electric charge charged during the time t1 balances electric charge discharged during the time t2. Thus, as shown in a circle located at an upper position of FIG. 1, the output voltage Vout includes slight ripples having a ripple voltage Vr, but assumes a substantially constant value. It is preferable that the frequency fp of the pulse signal Sc be set sufficiently high such that the ripple voltage Vr becomes smaller than the resolution of about 20 mV of the A/D converter circuit 19. In the present embodiment, as mentioned above, fp=2 kHz. Thus, even when the gas sensor element drive circuit 12 and the A/D converter circuit 19 (control circuit 13); i.e., the output terminal 18 and the A/D conversion input terminal 13AD, are directly connected, ripples do not cause variations in the A/D-converted value Dad, and manufacturing cost becomes low.

In order to remove ripples, the A/D converter circuit 19 may contain a low-pass filter (LPF; not shown) having a cut-off frequency lower than the frequency fp of the pulse signal Sc. Thus, ripples are removed from the output voltage Vout before the output voltage Vout undergoes A/D conversion. In this case, the cost of electronic components constituting the LPF is incurred. However, since noise which is superposed on the output voltage Vout can also removed, use of the LPF is particularly effective when the control system is used in a high noise environment such as a vehicle.

Figure 2:
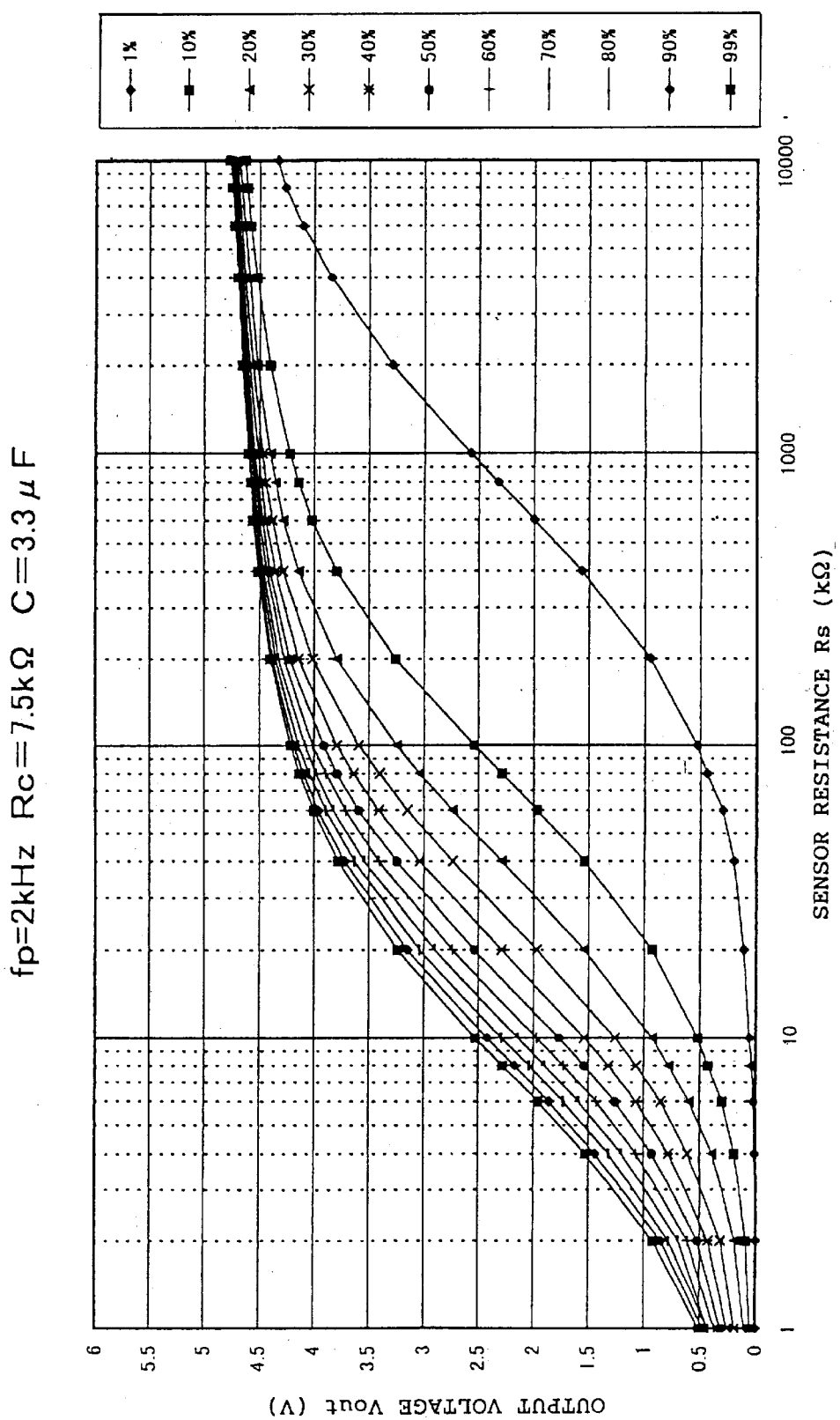
FIG. 2 is a graph showing variation in output voltage Vout at the operating point Pd in the control system of FIG. 1, when the sensor resistance Rs of the gas sensor element is changed, while the duty ratio of an input pulse signal is also changed as a parameter.
Figure 3:
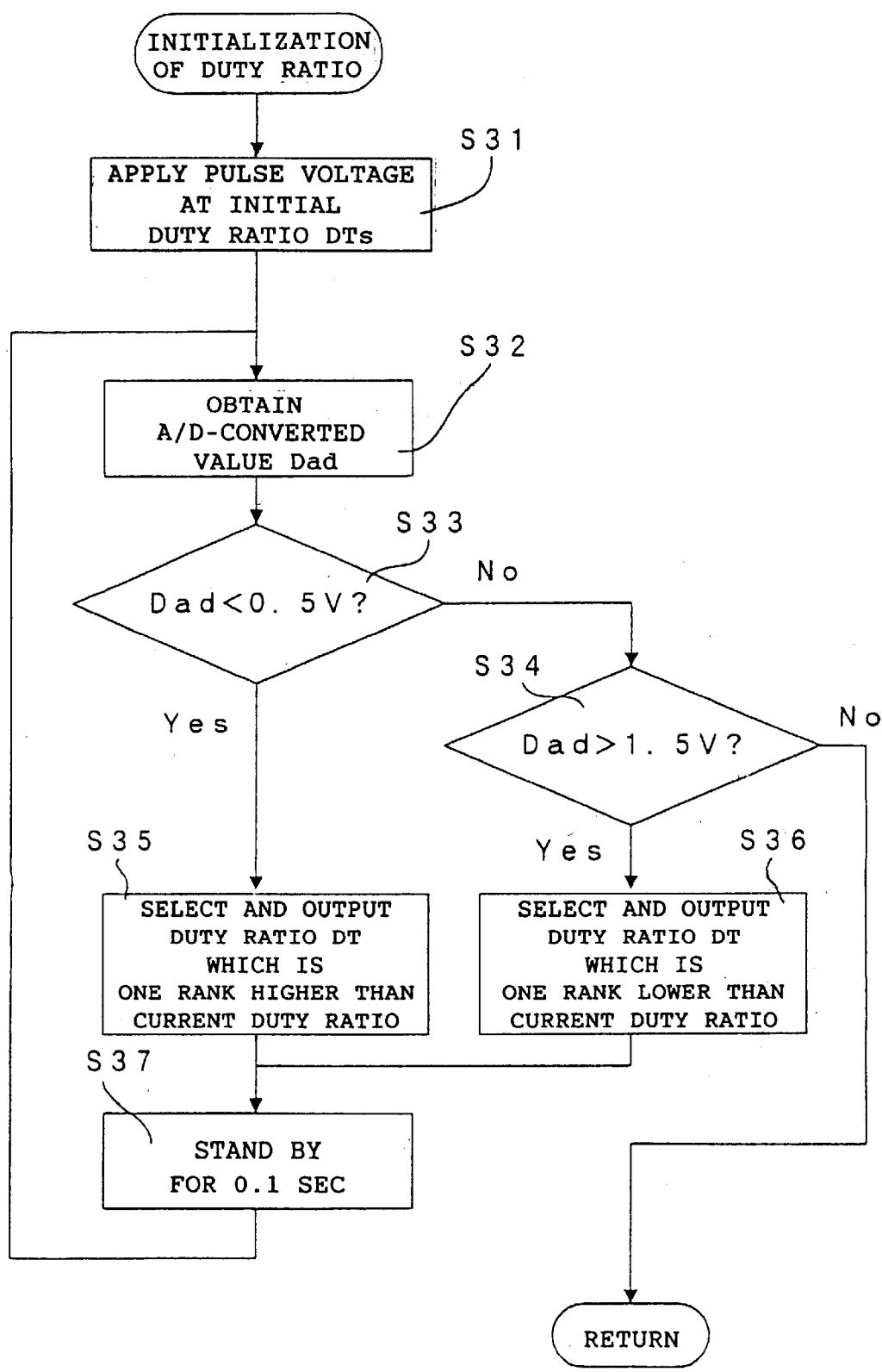
FIG. 3 is a flowchart showing the detail of a control performed by the control system of FIG. 1 for initializing an input pulse signal.

Next, FIG. 2 shows variation in the output voltage Vout (A/D-converted value Dad) associated with variation in the sensor resistance Rs of the gas sensor element 11 in the control system 10 including the gas sensor element drive circuit 12. The duty ratio DT (%) of the pulse signal Sc is used as a parameter. In actuality, the output voltage Vout was measured using the circuit of FIG. 1 in which a variable resistor was used in place of the gas sensor element 11.

As can be understood, even when the duty ratio DT of the pulse signal Sc is constant, as the sensor resistance Rs varies, the output voltage Vout varies. The reason for this is as follows. When the sensor resistance Rs increases, the discharge time constant τ2 increases; as a result, the discharge rate decreases. Therefore, the voltage across the capacitor 14 increases until electric charge charged during the time t1 balances electric charge discharged during the time t2.

As mentioned above, the frequency fp of the pulse signal is 2 kHz; the resistance Rc of the fixed resistor 15 is 7.5 kΩ; and the capacitance C of the capacitor 14 is 3.3 μF. As seen from the graph, when the duty ratio DT is rendered constant, the output voltage Vout increases monotonously and gently with the sensor resistance Rs. Accordingly, the sensor resistance Rs can be obtained from the output voltage Vout; i.e., the A/D-converted value Dad, which is obtained by A/D conversion of the output voltage Vout, and the duty ratio DT of an applied pulse signal.

As understood from the graph, even when the sensor resistance Rs varies over a range of several orders of magnitude (for example, three orders of magnitude ranging from 1 kΩ to 1 MΩ), measurement is possible.

Furthermore, this characteristic indicates, as mentioned previously, that, even when the sensor resistance of the gas sensor element varies greatly due to environmental factors, such as temperature or humidity, variation in the concentration of the specific gas can be detected accurately by varying the duty ratio DT of the pulse signal Sc to thereby vary the output voltage to an appropriate range.

For example, suppose that, when the pulse signal Sc having a duty ratio DT of 90% is input to the gas sensor element drive circuit 12, the sensor resistance Rs has varied to 100 kΩ or higher due to environmental factors. In this case, the output voltage Vout is biased to a high value of about 4.2 V. In this state, even when the sensor resistance Rs increases slightly due to a further increase in the concentration of the specific gas, variation in the output voltage Vout is small because of a gentle inclination of the graph curve. As a result, accurate detection of variation in the concentration of the specific gas is difficult.

By contrast, when the duty ratio DT of the pulse signal Sc is modified to 10%, the output voltage Vout becomes about 2.5 V, and the inclination of the graph curve increases. In this state, when the sensor resistance Rs increases slightly due to a further increase in the concentration of the specific gas, the output voltage Vout varies greatly. Thus, variation in the concentration of the specific gas can be detected accurately. In this manner, by varying of the duty ratio DT, the output voltage Vout can be maintained within a predetermined range, thereby enabling accurate detection of variation in the concentration of the specific gas.

Furthermore, even when sensor properties vary among the gas sensor elements 11, by varying the duty ratio DT of the pulse signal Sc, variations in sensor properties can be absorbed in measurement.

Next will be described a control flow in the control system 10 of the present embodiment for controlling the output voltage Vout (A/D-converted value Dad) to a predetermined range by varying the duty ratio DT of the pulse signal Sc.

A duty-ratio initialization process (see FIG. 3), which will be described below, is executed by interrupting a main routine (not described in detail) executed within the microcomputer 20, at the initial stage of operation of the control system 10. In the flow described below, control is performed such that the output voltage Vout (A/D-converted value Dad) falls within a range of 0.5 V to 1.5 V.

Upon start of the duty-ratio initialization process by interruption, first, in step S31, the control circuit 13 inputs the pulse signal Sc having an initial duty ratio DTs to the pulse input terminal 17 of the gas sensor drive circuit 12.

The initial duty ratio DTs may assume any appropriate value. However, since the prediction of the sensor resistance Rs at startup of the process is difficult because of environmental factors, such as temperature and humidity, the duty ratio DTs is preferably set to about 50% to thereby facilitate subsequent increase or decrease of the initial duty ratio DTs.

Next, in step S32, the control circuit 13 obtains the A/D-converted value Dad, which is an A/D-converted value of the output voltage Vout.

In step S33, the control circuit 13 judges whether or not the obtained A/D-converted value Dad is less than 0.5 V.

In the case of a No judgement, or Dad≧0.5 V, in step S33, the control circuit 13 proceeds to step S34. In step S34, the control circuit 13 judges whether or not the obtained A/D-converted value Dad is in excess of 1.5 V.

In the case of a No judgement, or Dad≦1.5 V, in step S34; i.e., in the case of 0.5 V≦Dad≦1.5 V, the control circuit 13 judges that initialization is completed, and thus returns to the main routine.

In step S33, when the Yes judgement is obtained; i.e., when the control circuit 13 judges that the A/D-converted value Dad is lower than 0.5 V, the control circuit 13 proceeds to step S35. In step S35, the control circuit 13 selects and outputs a duty ratio DT which is one rank higher, as the duty ratio DT of the pulse signal Sc. For example, the control circuit 13 selects a duty ratio DT which is one rank (for example, 1%) higher than the current duty ratio, and outputs the pulse signal Sc having the selected duty ratio DT. Thus, as understood from the graph of FIG. 2, the output voltage Vout (A/D-converted value Dad) increases accordingly.

Subsequently, the control circuit 13 proceeds to step S37. In step S37, the control circuit 13 stands by for 0.1 sec to wait until transient response caused by modification of the duty ratio DT settles. Then, the control circuit 13 returns to step S32 to repeat the same process. By repeating this process an appropriate number of times, the A/D-converted value Dad is modified so as to satisfy the relation 0.5 V≦Dad≦1.5 V. Thus, as described above, when the No judgement is obtained in step S34, the control circuit 13 judges that initialization is completed, and returns to the main routine.

In step S34, when a Yes judgement is obtained; i.e., when the control circuit 13 judges that the A/D-converted value Dad is in excess of 1.5 V, the control circuit 13 proceeds to step S36. In step S36, the control circuit 13 selects and outputs a duty ratio which is one rank lower, as the duty ration DT of the pulse signal Sc. For example, the control circuit 13 selects a duty ratio DT which is one rank (for example, 1%) lower than the current duty ratio, and outputs the pulse signal Sc having the selected duty ratio DT. Thus, the output voltage Vout (A/D-converted value Dad) decreases accordingly.

Subsequently, in a manner similar to that described above, the control circuit 13 proceeds to step S37. In step S37, the control circuit 13 stands by for 0.1 sec. Then, the control circuit 13 returns to step S32 to repeat the same process. By repeating this process an appropriate number of times, the A/D-converted value Dad is modified so as to satisfy the relation 0.5 V≦Dad≦1.5 V. Thus, initialization is completed, and the control circuit 13 returns to the main routine.

Figure 4:
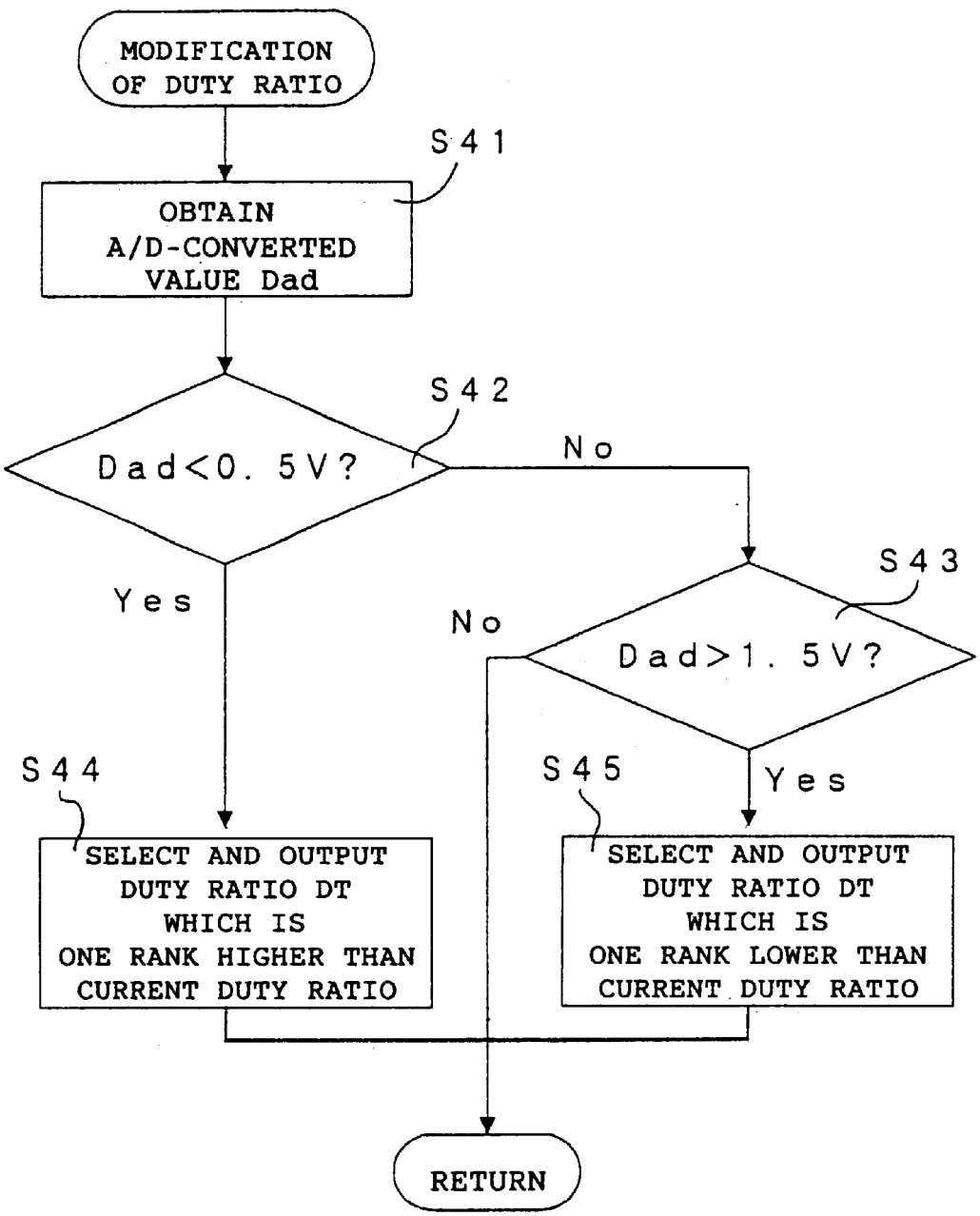
FIG. 4 is a flowchart showing the detail of a control performed by the control system of FIG. 1 for maintaining the output voltage Vout within a predetermined range in a normal drive state.

Next will be described with reference to FIG. 4 a control flow for controlling the output voltage Vout (A/D-converted value Dad) to a predetermined range (0.5 V to 1.5 V in the present embodiment) even when the sensor resistance Rs varies due to, for example, environmental factors, in a state that the control system 10 of the present embodiment is driven.

Upon start of the duty modification process by interruption, first, in step S41, the control circuit 13 obtains the A/D-converted value Dad.

In step S42, the control circuit 13 judges whether or not the obtained A/D-converted value Dad is less than 0.5 V.

In the case of a No judgement in step S42; i.e., Dad≧0.5 V, the control circuit 13 proceeds to step S43. In step S43, the control circuit 13 judges whether or not the obtained A/D-converted value Dad is in excess of 1.5 V.

In the case of a No judgement, or Dad≦1.5 V, in step S43; i.e., in the case of 0.5 V≦Dad≦1.5 V, the output voltage Vout falls within a predetermined range (0.5 V to 1.5 V). Therefore, modification of the duty ratio DT is not necessary, and thus the control circuit 13 returns to the main routine.

In step S42, when a Yes judgement is obtained; i.e., when the control circuit 13 judges the A/D-converted value Dad is lower than 0.5 V, the control circuit 13 proceeds to step S44. In step S44, the control circuit 13 selects and outputs a duty ratio DT which is one rank higher, as the duty ratio DT of the pulse signal Sc. For example, the control circuit 13 outputs the pulse signal Sc having a duty ratio DT which is one rank (for example, 1%) higher than the current duty ratio. Thus, as understood from the graph of FIG. 2, the output voltage Vout (A/D-converted value Dad) increases accordingly.

In step S43, when a Yes judgement is obtained; i.e., when the control circuit 13 judges that the A/D-converted value Dad is in excess of 1.5 V, the control circuit 13 proceeds to step S45. In step S45, the control circuit 13 selects and outputs a duty ratio which is one rank lower, as the duty ration DT of the pulse signal Sc, and subsequently returns to the main routine. For example, the control circuit 13 outputs the pulse signal Sc having a duty ratio DT which is one rank (1%) lower than the current duty ratio. Thus, the output voltage Vout (A/D-converted value Dad) decreases accordingly.

In the case of a great variation in the sensor resistance Rs of the gas sensor element, a one-rank modification of the duty ratio DT may not be sufficient for restoring the output voltage Vout to a predetermined range (0.5 V to 1.5 V). In this case, the duty modification process is again executed by interruption to thereby increase/decrease the duty ratio DT accordingly. Thus, the A/D-converted value Dad can be restored to the predetermined range (0.5 V to 1.5 V).

The present embodiment is described while mentioning a 1% interval between duty ratios DT which are different by one rank. However, a duty ratio can be selected as appropriate. For example, a duty ratio may be selected from among those which are arrayed at 0.5% or 2% intervals. Also, duty ratios from which selection is to be made may not be necessarily arrayed at equal intervals (at 1% intervals in the above embodiment), but may be arrayed at appropriate intervals. For example, duty ratios from which selection is to be made may be arrayed at equal-ratio intervals, such as . . . , 39.2%, 41.1%, 43.2%, 45.4%, 47.6%, 50.0%, 52.5%, 55.1%, 57.9%, 60.7%, 63.8%, . . . , (at intervals of a ratio of 1.05). In the graph shown in FIG. 2, for each parameter, a gap between graph curves increases as the duty ratio DT decreases. As understood from this phenomenon, when duty ratios are arrayed at equal-ratio intervals, an array of duty ratios can contain many small duty ratios, thereby enabling finer adjustment. Selectable values of the duty ratio DT may be stored in the ROM contained in the microcomputer 20.

As understood from the graph of FIG. 2, the relation ship between the sensor resistance Rs and the output voltage Vout (A/D-converted value Dad) is represented by a single graph curve selected in accordance with the duty ratio DT serving as a parameter. Accordingly, by selecting the duty ratio DT from among predetermined values as mentioned above and by retaining the relationship between the sensor resistance Rs and the A/D-converted value Dad for each duty ratio in the ROM of the microcomputer 20, the sensor resistance Rs can be immediately obtained from the A/D-converted value Dad. Thus, even when environmental variation arises, the output voltage Vout (A/D-converted value Dad) can be maintained within a range of 0.5 V to 1.5 V by means of the above-mentioned process. Therefore, variation in the concentration of the specific gas can be detected appropriately to thereby effectively control the electronic control assembly 21.

Figure 5:
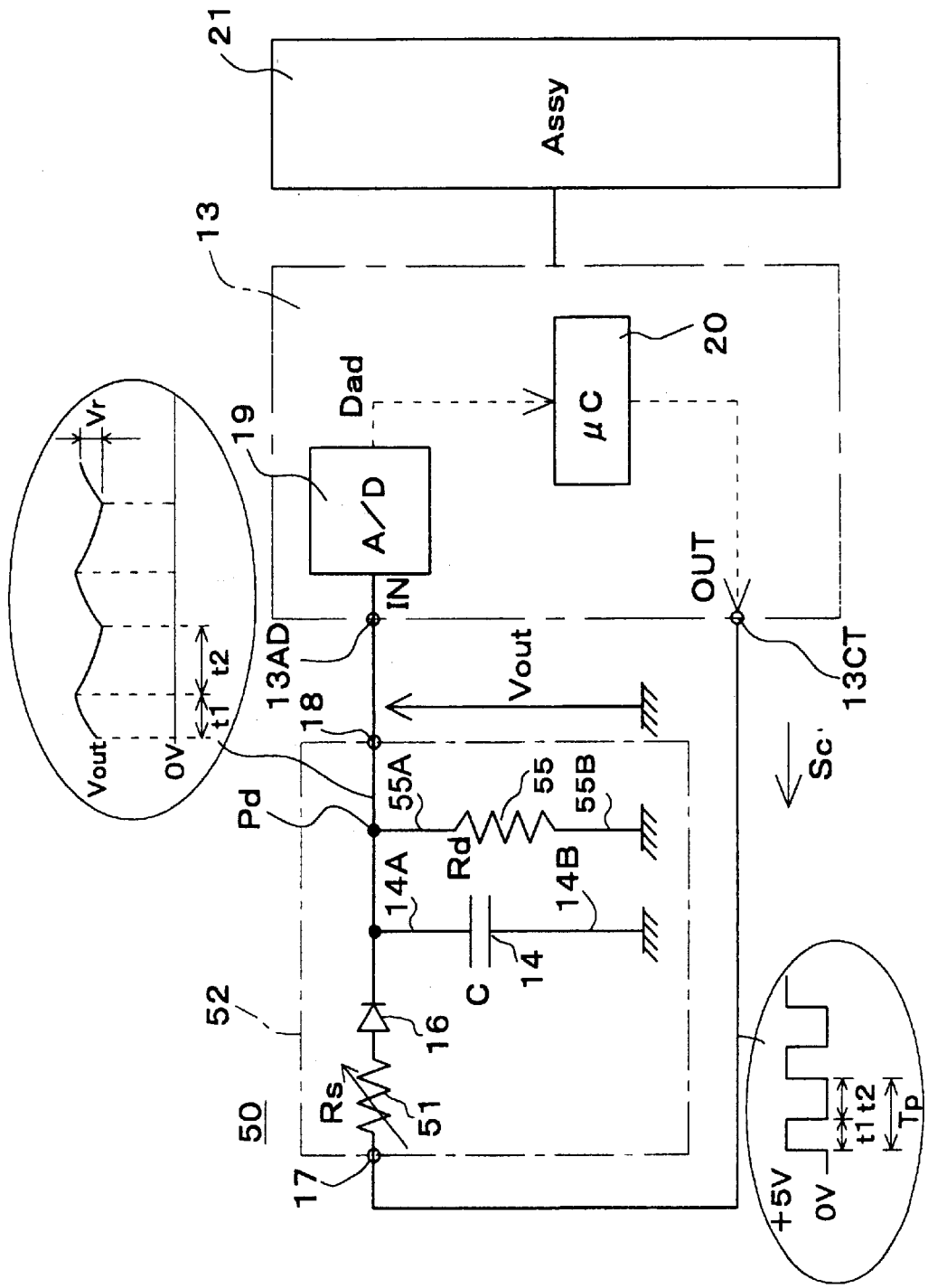
FIG. 5 is a circuit diagram and block diagram showing the configuration of a control system using a gas sensor drive circuit and a gas sensor element according to a second embodiment of the present invention.

Next, a second embodiment of the present invention will be described with reference to FIG. 5. A control system 50 of the present embodiment is equivalent to the control system of the first embodiment in which the gas sensor element 11 and the fixed resistor 15 in the gas sensor element drive circuit 12 are replaced with each other. Similar features are denoted by common reference numerals. Different features will be primarily described, and repeated description of similar features will be omitted or simplified.

As mentioned above, in a gas sensor element drive circuit 52 of the present embodiment, a gas sensor element 51 is connected between the pulse input terminal 17 and the diode 16, which is oriented such that the cathode thereof is located on the capacitor 14 side. A fixed resistor 55 having a resistance Rd of 7.5Ω is connected in parallel with the capacitor 14. Accordingly, when the pulse signal Sc output from the control output terminal 13CT of the control circuit 13 is input to the pulse input terminal 17, the capacitor 14 is charged via the gas sensor element 51 and the diode 16 during the period t1 when the pulse signal Sc is in the first potential state (high level, or +5 V). The charge stored in the capacitor 14 is discharged via the fixed resistor 55 during the period t2 when the pulse signal Sc is in the second potential state (low level, or 0 V).

Accordingly, a charging time constant $\tau 1$ is expressed as $\tau 1 = C \cdot Rd \cdot Rs/(Rd+Rs)$, and a discharging time constant $\tau 2$ is expressed as $\tau 2 = CRd$. As the sensor resistance Rs of the gas sensor element 51 increases, the charging rate decreases. Thus, the relationship between the sensor resistance Rs and the output voltage Vout is the inverse of that of the first embodiment. As in the case of the first embodiment, the operating point Pd whose potential varies with the sensor resistance Rs is located at one end 14A of the capacitor 14. The potential at the operating point Pd is fed to the output terminal 18.

Also, in the control system 50, the sensor resistance Rs of the gas sensor element 51 can be known from the output voltage Vout (A/D-converted value Dad). Thus, by obtaining the A/D-converted value Dad, variation in the concentration of a specific gas can be determined. Also, in the control system 50, the output voltage Vout (A/D-converted value Dad) increases with the duty ratio DT of the pulse signal Sc which is input to the pulse input terminal 17. Thus, even when the sensor resistance Rs of the gas sensor element 51 varies greatly due to an environmental factor, such as temperature or humidity, variation in the concentration of the specific gas can be detected accurately by varying the duty ratio DT of the pulse signal Sc to thereby vary the output voltage Vout to an appropriate range.

Accordingly, the electronic control assembly 21 can be controlled so as to open/close a flap according to a detected variation in the concentration of the specific gas.

The control system 50 of the present embodiment may also follow control flows similar to those of the first embodiment (see FIGS. 3 and 4) in order to vary the duty ratio DT of the pulse signal Sc so as to maintain the output voltage within a predetermined range. However, in contrast to the first embodiment, when the A/D-converted value Dad decreases below a predetermined range, a duty ratio which is one rank lower than the current duty ratio is selected in step S35 or S44 (see FIGS. 3 or 4). When the A/D-converted value Dad increases beyond the predetermined range, a duty ratio which is one rank higher is selected in step S36 or S45.

Figure 6:
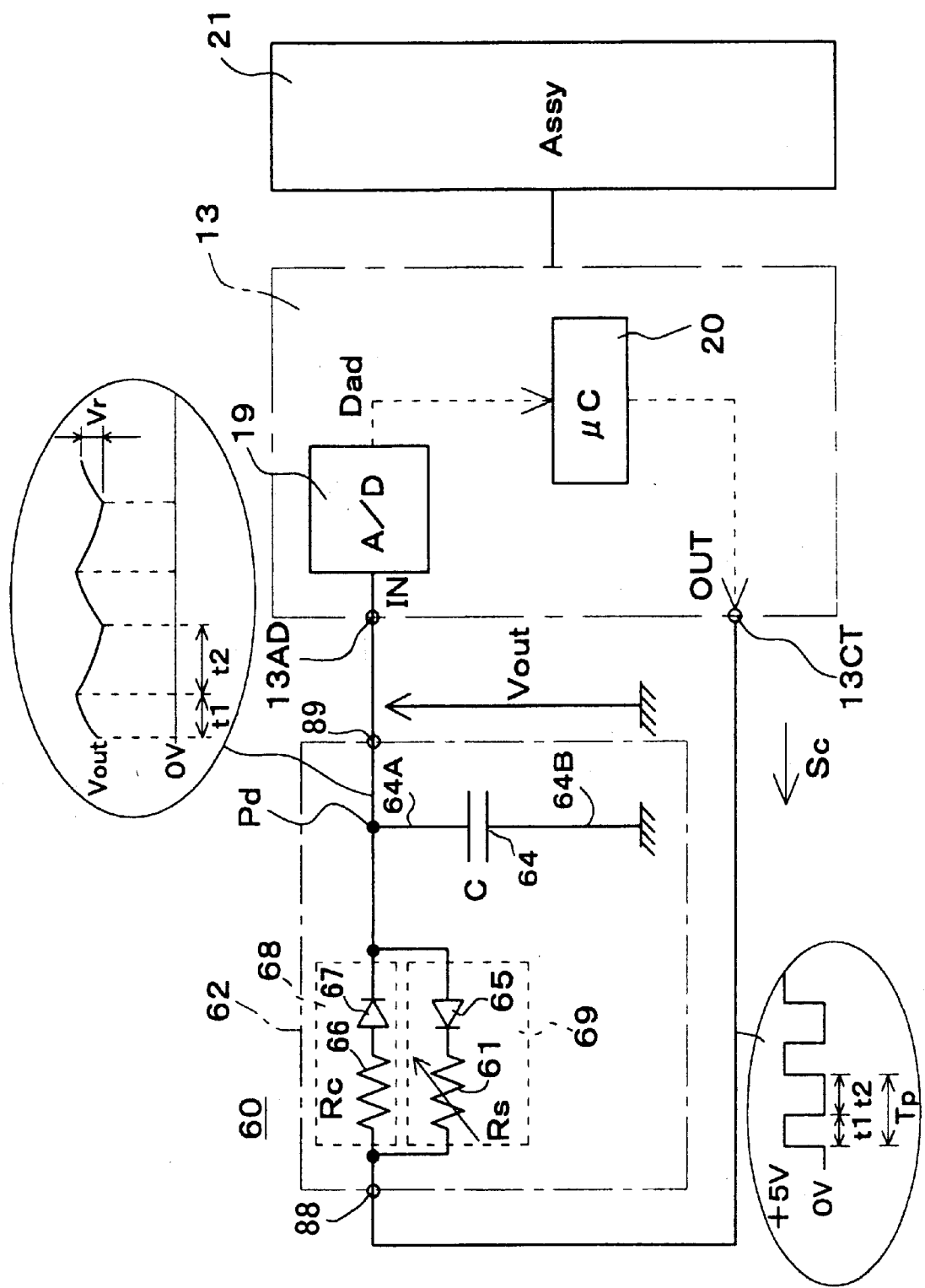
FIG. 6 is a circuit diagram and block diagram showing the configuration of a control system using a gas sensor drive circuit and a gas sensor element according to a third embodiment of the present invention.

Next, a third embodiment of the present invention will be described with reference to FIGS. 6 and 7. In the gas sensor element drive circuit 12 of the first embodiment, the capacitor 14 and the gas sensor element 11 are connected in parallel, and the capacitor 14 discharges via the gas sensor element 11. By contrast, in a gas sensor element drive circuit 62 of a control system 60 of the present embodiment, the charge stored in a capacitor 64 is returned or discharged to the control output terminal 13CT which assumes the ground potential (0 V), via a gas sensor element 61 and a second diode 65. Similar features are denoted by common reference numerals. Different features will be primarily described, and repeated description of similar features will be omitted or simplified.

As mentioned above, in the gas sensor element drive circuit 62 of the third embodiment, an RD series circuit 68 and an SD series circuit 69 are connected in parallel between a pulse input terminal (pulse input point) 88 and one end 64A of the capacitor 64. The other end 64B of the capacitor 64 is grounded. The RD series circuit 68 is configured in the following manner: a fixed resistor 66 having a resistance Rc of 7.5 kΩ and a first diode 67 which is oriented such that the cathode thereof is located on the capacitor 64 side are connected in series. The SD series circuit 69 is configured in the following manner: the gas sensor element 61 and the second diode 65 which is oriented such that the anode thereof is located on the capacitor 64 side are connected in series. The operating point Pd whose potential varies with the sensor resistance Rs is located at the one end 64A of the capacitor 64. The potential at the operating point Pd is fed to an output terminal 89.

When the pulse signal Sc output from the control output terminal 13CT of the control circuit 13 is input to the pulse input terminal 88 of the gas sensor element drive circuit 62, the capacitor 64 is charged via the RD series circuit 68, which is composed of the fixed resistor 66 and the first diode 67, during the period t1 when the pulse signal Sc is in the first potential state (high level, or +5 V). Thus, the fixed resistor 66 and the first diode 67 constitute a charging circuit. The charge stored in the capacitor 64 is discharged via the SD series circuit 69, which is composed of the second diode 65 and the gas sensor element 61, during the period t2 when the pulse signal Sc is in the second potential state (low level, or 0 V). Thus, the second diode 65 and the gas sensor element 61 constitute a discharging circuit.

A charging time constant (first time constant) $\tau 1$ is expressed as $\tau 1 = CRc$, and a discharging time constant (second time constant) $\tau 2$ is expressed as $\tau 2 = CRs$. As the sensor resistance Rs of the gas sensor element 61 increases, the discharge rate decreases; thus, the output voltage Vout increases. That is, the relationship between the sensor resistance Rs and the output voltage Vout is similar to that of the first embodiment.

However, in the first embodiment, a portion of charge flowing through the fixed resistor 15 is not used for charging the capacitor 14, but flows through the gas sensor element 11. Thus, charging efficiency is reduced accordingly. The charging voltage of the capacitor 14; i.e., the output voltage Vout, increases, at most; i.e., even at a duty ratio DT of 100%, up to the value "5 V×Rs·(Rc+Rs)" obtained through potential division by means of the fixed resistor 15 and the gas sensor element 11. In contrast, in the gas sensor element drive circuit 62 of the present embodiment, a charging path and a discharging path are separated from each other by means of two diodes 65 and 67, thereby achieving high charging efficiency and relatively high Vout. Particularly, even when the sensor Rs is low, a relatively high value of Vout can be obtained. Thus, the range of the sensor resistance Rs which the control system 60 can accommodate can be expanded downward.

Figure 7:
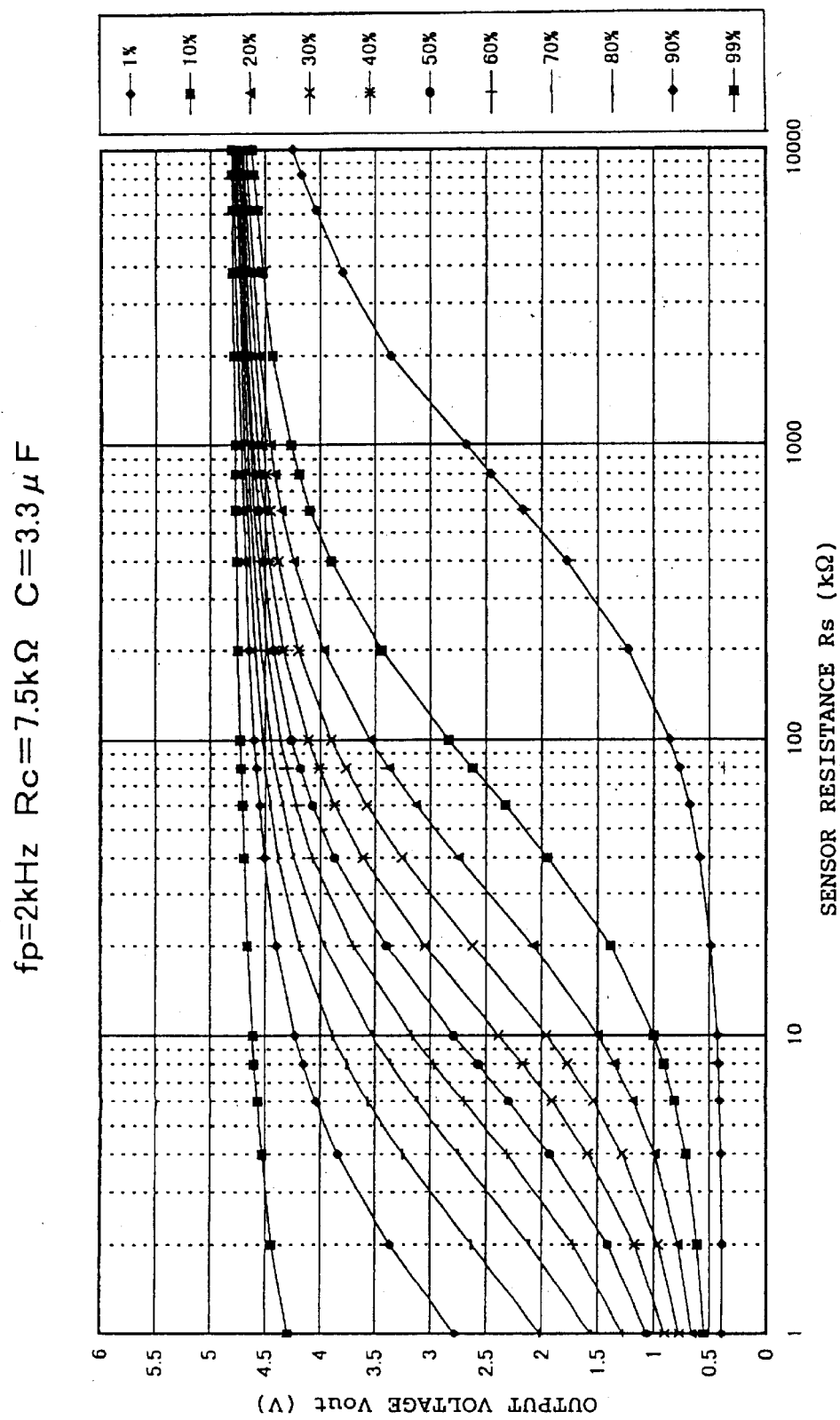
FIG. 7 is a graph showing variation in output voltage Vout at the operating point Pd in the control system of FIG. 6, when the sensor resistance Rs of the gas sensor element is changed, while the duty ratio of an input pulse signal is also changed as a parameter.

The above effect is apparent by comparing the graph of FIG. 7 with the graph of FIG. 2 associated with the control system 10 of the first embodiment. Specifically, a portion of the graph of FIG. 7 corresponding to high values of the sensor resistance Rs is substantially similar to that of the graph of FIG. 2. However, in contrast to the graph of FIG. 2, a portion of the graph of FIG. 7 corresponding to low values of the sensor resistance Rs exhibits sufficiently high Vout values. Even in a range of low values of the sensor resistance Rs (for example, in a range of Rs of 1 kΩ to 5 kΩ), a sufficiently large value of the output voltage Vout (Vout≧2.0 V) can be obtained by selecting a large duty ratio (for example, DT≧80%). Also, even in a range of the sensor resistance Rs not greater than 1 kΩ, variation in the concentration of the specific gas can be measured. By using the control system 60 (gas sensor element drive circuit 62) of the third embodiment, variation in the concentration of a gas can be detected for a sensor resistance which varies over a wider range.

Also, in the control system 60, the sensor resistance Rs of the gas sensor element 61 can be known from the output voltage Vout (A/D-converted value Dad). Thus, by obtaining the A/D-converted value Dad, variation in the concentration of the specific gas can be determined. Also, in the control system 60, the output voltage Vout (A/D-converted value Dad) increases with the duty ratio DT of the pulse signal Sc which is input to the pulse input terminal 88. Thus, even when the sensor resistance Rs of the gas sensor element varies greatly due to environmental factors, such as temperature or humidity, variation in the concentration of the specific gas can be detected accurately by varying the duty ratio DT of the pulse signal Sc to thereby vary the output voltage Vout to an appropriate range.

Accordingly, the electronic control assembly 21 can be controlled so as to open/close a flap according to a detected variation in the concentration of the specific gas.

The control system 60 of the present embodiment may also follow control flows similar to those of the first embodiment (see FIGS. 3 and 4) in order to vary the duty ratio DT of the pulse signal Sc so as to maintain the output voltage within a predetermined range.

In modifying of the duty ratio DT, a duty ratio may be selected from among those which are arrayed at equal intervals (for example, at 1% intervals). However, as apparent from the graph of FIG. 7, duty ratios from which selection is to be made may be arrayed such that a mutual interval is large among those duty ratios which are arrayed in the vicinity of a duty ratio of 50% and such that a mutual interval is small among large duty ratios and among small duty ratios. For example, duty ratios from which selection is to be made may be arrayed so as to decrease at a ratio of 1.05 with respect to 50% and so as to increase at a ratio of 1/1.05 with respect to 50%, such as . . . , 39.2%, 41.1%, 43.2%, 45.4%, 47.6%, 50.0%, 52.4%, 54.6%, 56.8%, 58.9%, 60.8%, . . . .

Figure 8:
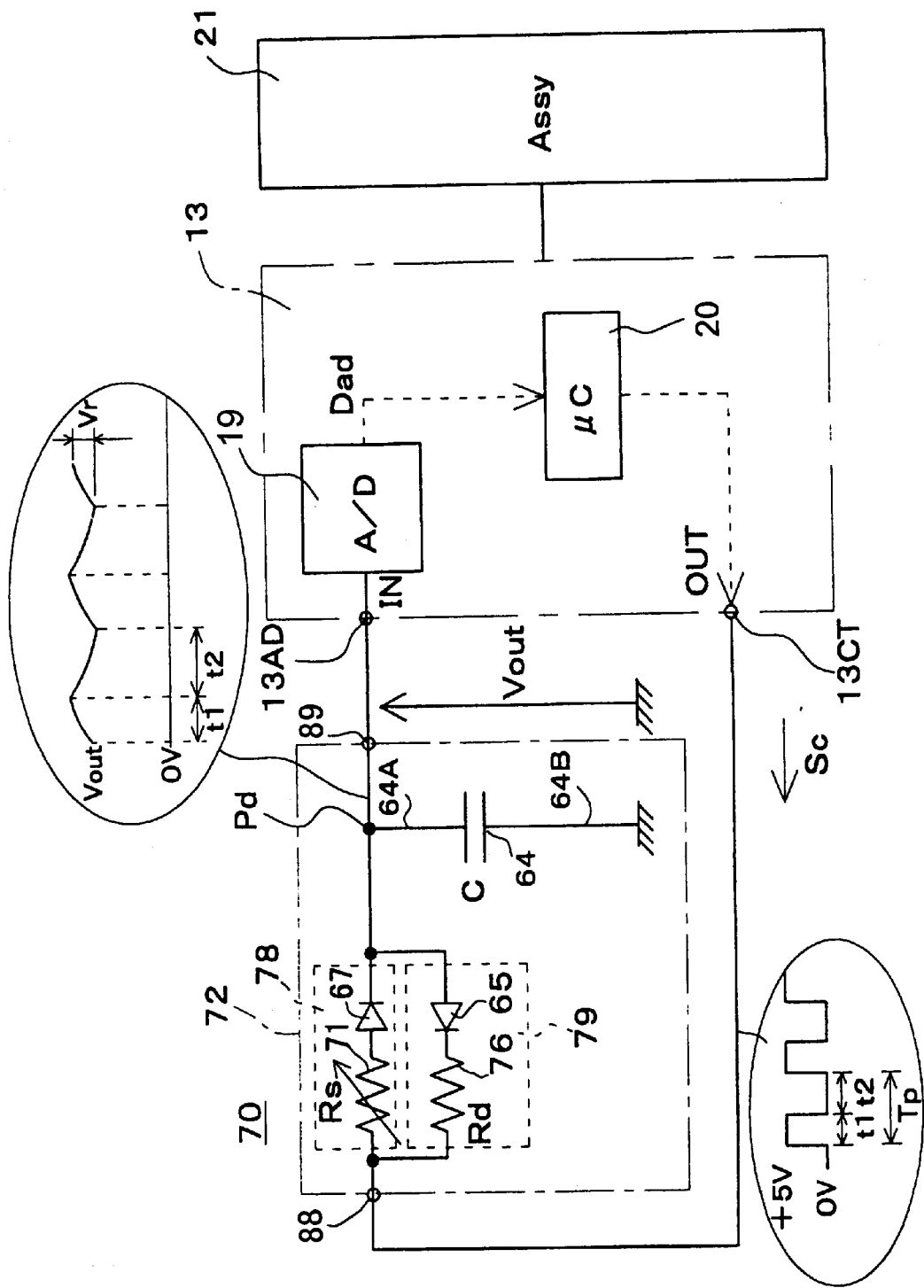
FIG. 8 is a circuit diagram and block diagram showing the configuration of a control system using a gas sensor drive circuit and a gas sensor element according to a fourth embodiment of the present invention.

Next, a fourth embodiment of the present invention will be described with reference to FIG. 8. A control system 70 of the present embodiment is equivalent to the control system of the third embodiment in which the gas sensor element 61 and the fixed resistor 66 in the gas sensor element drive circuit 62 are replaced with each other. Similar features are denoted by common reference numerals. Different features will be primarily described, and repeated description of similar features will be omitted or simplified.

As mentioned above, in a gas sensor element drive circuit 72 of the fourth embodiment, an SD series circuit 78 and an RD series circuit 79 are connected in parallel between a pulse input terminal 88 and one end 64A of the capacitor 64. The other end 64B of the capacitor 64 is grounded. The SD series circuit 78 is configured in the following manner: the gas sensor element 71 and a first diode 67 which is oriented such that the cathode thereof is located on the capacitor 64 side are connected in series. The RD series circuit 79 is configured in the following manner: a fixed resistor 76 having a resistance Rd of 7.5 kΩ and a second diode 65 which is oriented such that the anode thereof is located on the capacitor 64 side are connected in series. The operating point Pd whose potential varies with the sensor resistance Rs is located at the one end 64A of the capacitor 64. The potential at the operating point Pd is fed to an output terminal 89.

When the pulse signal Sc output from the control output terminal 13CT of the control circuit 13 is input to the pulse input terminal 88, the capacitor 64 is charged via the SD series circuit 78, which is composed of the gas sensor element 71 and the first diode 67, during the period t1 when the pulse signal Sc is in the first potential state (high level, or +5 V). Thus, the gas sensor element 71 and the first diode 67 constitute a charging circuit. The charge stored in the capacitor 64 is discharged via the RD series circuit 79, which is composed of the second diode 65 and the fixed resistor 76, during the period t2 when the pulse signal Sc is in the second potential state (low level, or 0 V). Thus, the second diode 65 and the fixed resistor 76 constitute a discharging circuit.

A charging time constant $\tau 1$ is expressed as $\tau 1 = CRs$, and a discharging time constant $\tau 2$ is expressed as $\tau 2 = CRd$. As the sensor resistance Rs of the gas sensor element 71 increases, the charging rate decreases; thus, the output voltage Vout decreases. That is, the relationship between the sensor resistance Rs and the output voltage Vout is the inverse of that of the third embodiment, and is thus similar to that of the second embodiment.

However, in the control system 50 of the second embodiment, a portion of charge flowing through the gas sensor element 51 is not used for charging the capacitor 14, but flows through the fixed resistor 55. Thus, charging efficiency is reduced accordingly. The charging voltage of the capacitor 14; i.e., the output voltage Vout, increases, at most; i.e., even at a duty ratio DT of 100%, up to the value "5 V×Rd·(Rd+Rs)" obtained through potential division by means of the gas sensor element 11 and the fixed resistor 15. In contrast, in the gas sensor element drive circuit 72 of the present embodiment, a charging path and a discharging path are separated from each other by means of two diodes 65 and 67, thereby achieving high charging efficiency and relatively high Vout. In contrast to the third embodiment, particularly, even when the sensor Rs is high, a relatively high value of Vout can be obtained. Thus, the range of the sensor resistance Rs which the control system 70 can accommodate can be expanded upwards.

Also, in the control system 70, the sensor resistance Rs of the gas sensor element 71 can be known from the output voltage Vout (A/D-converted value Dad). Thus, by obtaining the A/D-converted value Dad, variation in the concentration of the specific gas can be determined. Also, in the control system 70, the output voltage Vout (A/D-converted value Dad) increases with the duty ratio DT of the pulse signal Sc which is input to the pulse input terminal 88. Thus, even when the sensor resistance Rs of the gas sensor element varies greatly due to environmental factors, variation in the concentration of the specific gas can be detected accurately by varying the duty ratio DT of the pulse signal Sc to thereby vary the output voltage Vout to an appropriate range.

Accordingly, the electronic control assembly 21 can be controlled so as to open/close a flap according to a detected variation in the concentration of the specific gas.

The control system 70 of the present embodiment may also follow control flows similar to those of the first embodiment (see FIGS. 3 and 4) in order to vary the duty ratio DT of the pulse signal Sc so as to maintain the output voltage within a predetermined range. However, as in the case of the second embodiment, when the A/D-converted value Dad decreases below a predetermined range, a duty ratio which is one rank lower than the current duty ratio is selected in step S35 or S44 (see FIGS. 3 or 4). When the A/D-converted value Dad increases beyond the predetermined range, a duty ratio which is one rank higher is selected in step S36 or S45.

In modifying of the duty ratio DT, as is apparent from the graph of FIG. 7, duty ratios from which selection is to be made may be arrayed such that a mutual interval is large among those duty ratios which are arrayed in the vicinity of a duty ratio of 50% and such that a mutual interval is small among large duty ratios and among small duty ratios.

While the present invention has been described with reference to the first through fourth embodiments, the present invention is not limited thereto, but may be modified as appropriate without departing from the spirit or scope of the invention.

For example, the above embodiments are described while mentioning a gas sensor element whose sensor resistance Rs increases with the concentration of the specific gas (oxidizing gas such as NOx). However, the present invention is also applicable to the case where the specific gas is a reducing gas, such as hydrocarbon, and a gas sensor element to be used exhibits a characteristic that, as the concentration of the specific gas increases, the sensor resistance Rs thereof decreases.

The above embodiments are described while mentioning the A/D converter circuit 19 and the microcomputer 20, which are discrete. However, the A/D converter circuit may be incorporated into the microcomputer. In this case, an analog voltage (output voltage Vout) input to an analog input port is A/D-converted within the microcomputer, to thereby obtain a digital value (A/D-converted value Dad) for use in various processes.

As mentioned above, the control systems 10 and 50 of the first and second embodiments are slightly narrower in a measurable range of the sensor resistance Rs than the control systems 60 and 70 of the third and fourth embodiments, but have merit in that cost can be lowered because the second diode 65 is not needed. The selector from among the control systems 10, 50, 60, and 70 may be determined in consideration of a variation range of the sensor resistance Rs of a gas sensor element.

This application is based on Japanese Patent Application No. 2000-51636 filed Feb. 28, 2000, the disclosure of which is incorporated herein by reference in its entirety.

What is claimed is:

1. A control system for a gas sensor element having a sensor resistance which varies with the concentration of a specific gas, comprising:

a pulse input point into which a pulse signal is input, said pulse signal comprising a repetitive waveform having a first potential state and a second potential state;

a capacitor;

a charging circuit for charging said capacitor via a charge resistor during a period when the pulse signal in the first potential state is input to said pulse input point; and a discharging circuit for discharging said capacitor via a discharge resistor during a period when the pulse signal in the second potential state is input to said pulse input point;

said gas sensor element comprising at least either the charge resistor of said charging circuit or the discharge resistor of said discharging circuit, and at least either a charging current of said charging circuit or discharging current of said discharging circuit varying with the sensor resistance of the gas sensor element; and said control system further comprising:
- a control circuit comprising:
  - a microcomputer; and
  - an A/D converter circuit for converting a potential at an operating point located at one end of said capacitor to a digital value, which potential varies with the sensor resistance of the gas sensor element;
  - said control circuit being connected to said pulse input point and outputting the pulse siggal.

2. The control system as claimed in claim 1,
wherein either the first potential state or the second potential state is a ground potential state, and
the other state is a positive potential state, which is higher in potential than the ground potential.

3. The control system as claimed in claim 1, wherein the control circuit further comprises:
- output range judgement means for judging whether or not an A/D-converted value produced in the A/D converter circuit falls outside a predetermined range; and
- duty ratio modification means for modifying the duty ratio of the pulse signal such that the A/D-converted value falls within the predetermined range.

4. The control system as claimed in claim 1, wherein:
said charging circuit charging said capacitor at a first time constant via a charge resistor during a period when the pulse signal in the first potential state is input to said pulse input point,
said gas sensor element comprising the charge resistor,
said discharging circuit discharging said capacitor at a second time constant via a discharge resistor during a period when the pulse signal in the second potential state is input to said pulse input point, and
said A/D converter circuit receiving a potential at an operating point located at one end of said capacitor, which potential varies with the sensor resistance of the gas sensor element.

5. The control system as claimed in claim 1, wherein:
said charging circuit charging said capacitor at a first time constant via the gas sensor element and a diode during a period when the pulse signal in the first potential state is input to said pulse input point,
said discharging circuit discharging said capacitor at a second time constant via a resistor during a period when the pulse signal in the second potential state is input to said pulse input point,
said A/D converter circuit receiving a potential at an operating point located at one end of said capacitor, which potential varies with the sensor resistance of the gas sensor element, and
said control circuit being connected to said pulse input point of said charging circuit and outputting the pulse signal.

6. The control system as claimed in claim 1, wherein:
said charging circuit charging said capacitor at a first time constant via a RD series circuit comprising a resistor and a first diode, which is connected to the resistor in series, during a period when the pulse signal in the first potential state is input to said pulse input point,
said discharging circuit discharging said capacitor at a second time constant via a SD series circuit comprising the gas sensor element and a second diode, which is connected to the gas sensor element in series, and connected to the RD series circuit in parallel, during a period when the pulse signal in the second potential state is input to said pulse input point,
said A/D converter circuit receiving a potential at an operating point located at one end of said capacitor, which potential varies with the sensor resistance of the gas sensor element, and
said control circuit being connected to said pulse input point of said charging circuit and outputting the pulse signal.

7. The control system as claimed in claim 1, wherein:
said charging circuit charging said capacitor at a first time constant via a SD series circuit comprising the gas sensor element and a first diode, which is connected to the gas sensor element in series, during a period when the pulse signal in the first potential state is input to said pulse input point,
said discharging circuit discharging said capacitor at a second time constant via a RD series circuit comprising a resistor and a second diode, which is connected to the resistor in series, and connected to the SD series circuit in parallel, during a period when the pulse signal in the second potential state is input to said pulse input point,
said A/D converter circuit receiving a potential at an operating point located at one end of said capacitor, which potential varies with the sensor resistance of the gas sensor element, and
said control circuit being connected to said pulse input point of said charging circuit and outputting the pulse signal.

8. A control system for a gas sensor element having a sensor resistance which varies with the concentration of a specific gas, comprising:
- a pulse input point into which a pulse signal is input, said pulse signal comprising a repetitive waveform having a first potential state and a second potential state;
- a capacitor;
- a charging circuit for charging said capacitor at a first time constant via a charge resistor during a period when the pulse signal in the first potential state is input to said pulse input point;
- a discharging circuit for discharging said capacitor at a second time constant via a discharge resistor during a period when the pulse signal in the second potential state is input to said pulse input point,
- said gas sensor element comprising the discharge resistor, and
- the second time constant varying with the sensor resistance; and
- a control circuit comprising:
  - a microcomputer; and
  - an A/D converter circuit receiving a potential at an operating point located at one end of said capacitor, which potential varies with the sensor resistance of the gas sensor element; and
  - said control circuit being connected to said pulse input point and outputting the pulse signal.

9. The control system as claimed in claim 8,
wherein either the first potential state or the second potential state is a ground potential state, and
the other state is a positive potential state, which is higher in potential than the ground potential.

10. The control system as claimed in claim 8, wherein the control circuit further comprises:
- output range judgement means for judging whether or not an A/D-converted value produced in the A/D converter circuit falls outside a predetermined range; and duty ratio modification means for modifying the duty ratio of the pulse signal such that the A/D-converted value falls within the predetermined range.

11. A control system for a gas sensor element having a sensor resistance which varies with the concentration of a specific gas, comprising:

a pulse input point into which a pulse signal is input, said pulse signal comprising a repetitive waveform having a first potential state and a second potential state;

a capacitor;

a charging circuit for charging said capacitor at a first time constant via a resistor and a diode during a period when the pulse signal in the first potential state is input to said pulse input point;

a discharging circuit for discharging said capacitor at a second time constant via the gas sensor element during a period when the pulse signal in the second potential state is input to said pulse input point; and a control circuit comprising:
 a microcomputer; and
 an A/D converter circuit receiving a potential at an operating point located at one end of said capacitor, which potential varies with the sensor resistance of the gas sensor element; and said control circuit being connected to said pulse input point of said charging circuit and outputting the pulse signal.

12. The control system as claimed in claim 11, wherein either the first potential state or the second potential state is a ground potential state, and the other state is a positive potential state, which is higher in potential than the ground potential.

13. The control system as claimed in claim 11, wherein the control circuit further comprises:

output range judgement means for judging whether or not an A/D-converted value produced in the A/D converter circuit falls outside a predetermined range; and duty ratio modification means for modifying the duty ratio of the pulse signal such that the A/D-converted value falls within the predetermined range.

* * * * *